US006899892B2

(12) United States Patent
Gallaher et al.

(10) Patent No.: US 6,899,892 B2
(45) Date of Patent: May 31, 2005

(54) METHODS TO REDUCE BODY FAT

(75) Inventors: Daniel D. Gallaher, Roseville, MN (US); Laura Freiburger, St. Paul, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 90 days.

(21) Appl. No.: 10/025,633

(22) Filed: Dec. 19, 2001

(65) Prior Publication Data

US 2003/0124170 A1 Jul. 3, 2003

(51) Int. Cl.[7] .......................... A61K 47/00; A61K 9/00; A61K 7/00
(52) U.S. Cl. .................. 424/439; 424/400; 424/401
(58) Field of Search .................. 424/400, 401, 424/439

(56) References Cited

U.S. PATENT DOCUMENTS

| 3,388,082 A | 6/1968 | Rogers et al. ............... 260/17 |
| 3,627,872 A | 12/1971 | Parkinson ................... 424/79 |
| 4,432,968 A | 2/1984 | Page et al. |
| 5,576,306 A | 11/1996 | Dressman et al. |
| 5,585,366 A | 12/1996 | Gallaher et al. |
| 5,721,221 A | 2/1998 | Gallaher et al. |
| 5,756,461 A | 5/1998 | Stephens |
| 5,773,416 A | 6/1998 | Chehab |
| 5,780,258 A | 7/1998 | de la Brousse et al. |
| 5,789,393 A | 8/1998 | Dressman et al. |
| 5,919,902 A | 7/1999 | Becker et al. |
| 5,965,521 A | 10/1999 | Stephens et al. |
| 5,972,621 A | 10/1999 | Tartaglia et al. |
| 6,001,816 A | 12/1999 | Morsy et al. |
| 6,007,988 A | 12/1999 | Choo et al. ................... 435/6 |
| 6,020,324 A | 2/2000 | Jamas et al. |
| 6,048,837 A | 4/2000 | Friedman et al. |
| 6,124,439 A | 9/2000 | Friedman et al. |
| 6,143,731 A * | 11/2000 | Jamas et al. ................... 514/54 |
| 6,251,433 B1 | 6/2001 | Zuckermann et al. |
| 2002/0019334 A1 * | 2/2002 | Portman ......................... 514/2 |
| 2003/0013679 A1 | 1/2003 | Wolf et al. ................... 514/54 |
| 2003/0039708 A1 * | 2/2003 | Fleischner ................... 424/729 |

FOREIGN PATENT DOCUMENTS

| EP | 0502666 | 9/1992 | |
| WO | WO 9850398 A1 * | 11/1998 | ............ C07H/1/00 |

OTHER PUBLICATIONS

Abstract, Leptin in finctional hypothalamic amenorrhea, Andrico et al, Aug. 2002. vol. 17, Iss. 8; p. 2043.*
Bouche, Clara, et al., "Five–Week, Low–Glycemic Index Diet Decreases Total Fat Mass and Improves Plasma Lipid Profile inModerately Overweight Nondiabetic Men", *Diabetes Care*, vol. 25, No. 5, May 2002, Clinical Care/Education/Nutrition (Original Article), 822–828.
Kamphuis, MMJW, et al., "The effect of conjugated linoleic acid supplementation after weight loss on body weight regain, body composition, and resting metabolic rate in overweight subjects", *International Journal of Obesity*, 27, (2003),840–847.

(Continued)

*Primary Examiner*—Thurman K. Page
*Assistant Examiner*—Humera N. Sheikh
(74) *Attorney, Agent, or Firm*—Schwegman, Lundberg, Woessner & Kluth, P.A.

(57) ABSTRACT

The invention provides methods and compositions for reducing the percentage of body fat in a mammal and/or the level of leptin in the bloodstream of the mammal. Such methods involve administering to the mammal a diet containing viscous polysaccharides.

29 Claims, 4 Drawing Sheets

OTHER PUBLICATIONS

Larsen, Thomas M., et al., "Efficacy and safety of dietary supplements containing Conjugated Linoleic Acid (CLA) for the treatment of obesity—evidence from animal and human studies", *JLR Papers in Press. Published on Aug. 16, 2003 as Manuscript R300011–JLR200*, Copyrighted 2003 by Lipid Research, Inc.,(2003),1–23.

Pawlak, Dorota B., et al., "High Glycemic Index Starch Promotes Hypersecretion of Insulin and Higher Body Fat in Rats without Affecting Insulin Sensitivity", *American Society for Nutritional Sciences (Manuscript)*, Manuscript received May 30, 2000, Initial review completed Aug. 7, 2000, Revisions accepted Oct. 17, 2000,99–104.

Toda, Toshitaka, et al., "Change in Body Fat, But Not Body Weight or Metabolic Correlates of Obesity, Is related To symptomatic Relief of Obese Patients with Knee Osteoarthritis After a Weight Control Program", *The Journal of Rheumatology*, vol. 25, No. 11, (1998), 2181–2186.

Ducy, P., et al., "The Osteoblast: A Sophisticated Fibroblast Under Central Surveillance", *Science*, vol. 289, 15011504, (Sep. 1, 2000).

Fried, S.K., et al., "Symposium: Adipocyte Function, Differentiation and Metabolism—Regulatin of Leptin Production in Humans", *American Society for Nutritional Sciences*, 3127S–3131S.

Frigard, T., et al., "Fiber–Degrading Enzyme Increases Body Weight and Total Serum Cholesterol in Broiler Chickens Fed a Rye–Based Diet1,2", *The Journal of Nutrition, Official Publication of the American Institute of Nutrition*, vol. 124, No. 12, 2422–2430, (Dec. 1994).

Gallaher, C.M., et al., "Cholesterol Reduction by Glucomannan and Chitosan is Mediated by Changes in Cholesterol Absorption and Bile Acid and Fat Excretion in Rats", *American Society for Nutritional Sciences*, 2753–2759, (2000).

Gallaher, D.D., et al., "Relationships between Viscosity of Hydroxypropyl Methylcellulose and Plasma Cholesterol in Hamsters", *Nutrient Metabolism*, 1732–1738, (Sep. 9, 1992).

Gallaher, D.D., et al., "Viscosity and Fermentability as Attributes of Dietary Fiber Responsible for the Hypocholesterolemic Effect in Hamsters1–3", *American Institute of Nutrition*, 244–252, (Apr. 14, 1992).

Nightingale, J.S., "Lipid Binding From Aqueous Solution by Lipid Conjugated Hydroxyproplmethylcellulose", *Ph.D., Thesis, University of Washington*, 1–163, (1988).

Topping, D., "Hydroxyproplmethylcellulose, Viscosity, and Plasma Cholesterol Control", *Nutrition Reviews*, vol. 52, No. 5, 176–178.

Topping, D.L., et al., "A Viscous Fibre (Methylcellulose) Lowers Blood Glucose and Plasma Triacyglycerols and Increases Liver Glycogen Independently of Volatile Fatty Acid Production in the rat", *British Journal of Nutrition* (1988), 59, 21–30, 21–30, (Mar. 10, 1987).

\* cited by examiner

METHODS TO REDUCE BODY FAT

FIELD OF THE INVENTION

The present invention relates to the use of non-nutritive, viscous polysaccharides to reduce the percentage of body fat and the level of leptin in mammals. Examples of such polysaccharides include water-soluble cellulose-like polysaccharides such as β-glucans and hydroxypropyl methylcellulose.

BACKGROUND OF THE INVENTION

Obesity affects an ever-increasing proportion of the population of Western cultures. Nearly one-third of adults in the United States are in excess of their ideal body weight by at least 20%. Obesity has become a major public health problem, at least in part because it is associated with other health problems such as hypertension, elevated blood lipids, coronary artery disease, osteoarthritis and Type II or non-insulin-dependent diabetes mellitus (NIDDM). In the United States alone, there are an estimated 6–10 million individuals with NIDDM, including 18% of the population over 65 years of age and most of these individuals are obese (Harris et al. Diabetes 36:523–534, 1987).

According to conventional wisdom, stability in body composition requires that energy intake equals expenditure, at least over a prolonged period of time. Such wisdom therefore requires that obese persons reduce their food intake in order to reduce their weight and their percent body fat. However, while reduction of caloric intake can lead to short-term weight loss, the lost weight is often regained. Moreover, some evidence indicates that prolonged fluctuation of body weight can lead to weight increases and to increased body fat content.

It appears that there may be a signaling system that adjusts appetite, and accordingly food intake, to preserve a constant total adipose tissue mass. The nature of this signaling system has been examined in a variety of animal experiments involving induced weight change (Cohn et al., Yale J. Biol. Med. 34:598–607, 1962; Harris et al., Proc. Soc. Exp. Biol. Med. 191:82–89, 1989; and Wilson et al., Am. J. Physiol. 259: R1148–R1155, 1990); lipectomy (Forger et al., Metabolism 37:782–86, 1988; Liebelt et al., Ann. N.Y. Acad. Sci. 131:559–82, 1965; and Chlouverakis et al., Metabolism 23:133–37, 1974); plasma transfer from obese or satiated animals to hungry animals (Davis et al., Science 156:1247–48, 1967; Davis et al., J. Comp. Physiol. Psychol. 67:407–14, 1969; and King, Physiol. Psychol. 4:405–08, 1976); and parabiosis between obese and lean animals (Hervey, J. Physiol. 145:336–52, 1959; Parameswaran et al., Am. J. Physiol. 232:R150–R157, 1977; Nishizawa et al., Am. J. Physiol. 239:R344–351, 1980; Harris et al., Am. J. Physiol. 257: R326–R336, 1989; Schmidt et al., Acta Physiol. Acad. Sci. Hung. Tomus 36:293–98, 1969; Coleman et al., Diabetologia 9:294–98, 1973; Harris et al., Int. J. Obesity 11:275–83, 1987; and Coleman et al., Am. J. Physiol. 217:1298–1304, 1969).

Such studies may have identified certain factors that are involved in regulating obesity and body fat content, but confusion exists as to how to use such information to treat obesity. For example, Fried et al., 130 J. Nutr. 3127S–3131S (2000) has disclosed that serum leptin levels are usually elevated in obesity, indicating that lower serum levels of leptin may be beneficial for treating obesity. However, earlier animal data indicated that a leptin deficiency might lead to obesity. Mice that have homozygous mutant ob genes (ob/ob) have been reported to be obese but when given daily injections of recombinant leptin, their food intake was markedly inhibited and they experienced a reduction in body weight and fat. It is known that leptin is a protein expressed by the ob gene and that it is secreted by adipose tissue. Some researches have provided data indicating that leptin is a satiety factor and a regulator of metabolism (Levin et al., 1996 Proc. Natl Acad. Sci. USA 93:1726–1730). Hence, the relationship between leptin levels and body fat has been contradictory. See also, Pelleymounter et al., 1995, Science 269:540–543; Halaas et al., 1995 Science 269: 543–546; and Campfield et al., 1995 Science 269:546–549.

A number of studies have been conducted on the role of dietary fiber in health and disease. Some studies comparing the effects of various fiber sources on cholesterol have concluded that soluble cellulose-like materials reduce cholesterol levels. For example, U.S. Pat. Nos. 5,585,366 and 5,721,221 to Gallaher et al. disclose methods for reducing cholesterol levels in mammalian blood by administering high viscosity water-soluble cellulose derivatives such as hydroxypropyl methylcellulose. U.S. Pat. No. 6,020,324 to Jamas et al. discloses dietary supplements containing intact whole β-glucan in an amount sufficient to lower serum cholesterol levels. However, these patents do not provide treatments for reducing body fat.

Current weight loss treatment regimens generally either have negative side effects or are not particularly effective. Accordingly, a new approach is needed to regulating body fat content.

SUMMARY OF THE INVENTION

The invention provides methods and compositions for reducing the percentage of body fat in a mammal and the level of leptin in the bloodstream of a mammal comprising administering a sufficient amount of viscous, water-soluble, non-nutritive, non-starch, indigestible polysaccharide to the mammal for a time sufficient to reduce the percentage of body fat in the mammal. Such polysaccharides are polymers of monosaccharides substantially connected by beta (β) glycosidic linkages. The monosaccharides can be arabinose, fructose, glucose, glucosamine, glucuronic acid, galactose, galactosammine, mannose, N-acetylmuramic acid, N-acetylneuraminic acid, rhamnose, xylose or a mixture thereof. The beta glycosidic linkages are 1→2 beta-glycosidic bonds, 1→3 beta-glycosidic bonds, 1→4 beta-glycosidic bonds, 1→6 beta-glycosidic or a mixture thereof Examples of polysaccharides contemplated by the invention include locust bean gum, guar gum, carrageenan, alginate, modified cellulose, beta-glucan, or glucomannan.

In one embodiment, the polysaccharide has Formula I:

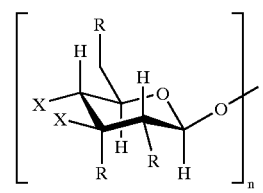

wherein
each R is separately hydroxy, lower alkyloxy, or hydroxy (lower(alkyloxy));
n is an integer ranging from about 500 to about 2500; and
X is an R group or a covalent bond to the oxygen at the first position of the adjacent monosaccharide.

Such polysaccharides can also be methylcellulose, hydroxypropyl methylcellulose, 2-hydroxypropyl methylcellulose, 2-hydroxyethyl methylcellulose, 2-hydroxybutyl methylcellulose, 2-hydroxyethyl ethylcellulose, 2-hydroxypropyl cellulose, methyl ethylcellulose, or 2-hydroxyethylcellulose.

Preferred polysaccharides are β-glucan and hydroxypropyl methylcellulose.

The compositions and polysaccharides of the invention can be administered or incorporated into a foodstuff. For example, the compositions and polysaccharides of the invention can be administered or incorporated into the an applesauce, a cereal, a cookie, a cracker, a flavored drink, a fruit juice, an ice cream, a milk shake, a pudding or a snack bar.

An example of a sufficient amount of polysaccharide is an amount that provides an intestinal viscosity of about 1000 mPa·s to about 3000 mPa·s, preferably about 1500 mPa·s to about 2500 mPa·s.

An example of a sufficient amount of polysaccharide to be administered or consumed is about 1 g to about 5 g polysaccharide per meal, preferably about 2 g to about 3 g polysaccharide per meal. A time sufficient for reducing the percentage of body fat is at least about two to at least about ten weeks, preferably at least about three weeks to at least about eight weeks, more preferably at least about four to at least about six weeks. However, the polysaccharide or composition thereof can be administered indefinitely.

In one embodiment, the percentage of body fat is reduced by about 5% to about 40%, preferably 10% to about 30%, more preferably about 15% to about 25%.

DETAILED DESCRIPTION OF THE INVENTION

Figure 1:
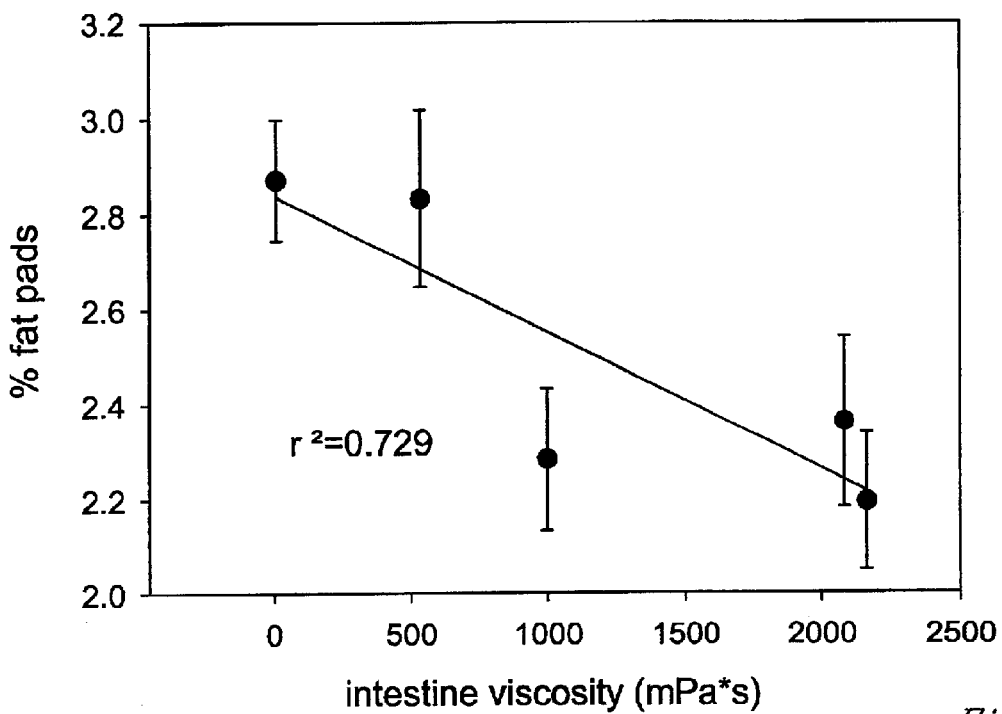
FIG. 1 graphically illustrates the relationship between the percent of fat mass and the viscosity of a supernatant of the intestinal contents of rats. As illustrated, there is a negative correlation between the intestinal viscosity and the percent fat mass, indicating that percent body fat decreases as the viscosity of the diet increases.

The present invention provides methods and compositions for reducing the percentage of body fat and/or the serum levels of leptin in a mammal by administering a viscous polysaccharide. In general, the viscous polysaccharides of the invention are water-soluble, non-nutritive, non-starch-like and indigestible. High viscosity polysaccharides are often very useful for reducing the percentage of body fat and for lowering leptin levels in the blood. However, it is the viscosity of the water-soluble fraction of the intestinal contents that is most important for achieving optimal reduction in body fat and leptin levels. Accordingly, a lower viscosity polysaccharide can be administered so long as the amount administered provides sufficient viscosity within the soluble portion of the intestinal contents.

Any water-soluble, non-nutritive, indigestible, non-starch, viscous polysaccharide available to one of skill in the art can be used in the compositions and methods of the invention. The viscous polysaccharides employed in this invention are further characterized in that they are non-toxic, non-ionic, non-caloric, biologically inert but edible. Examples of viscous polysaccharides that can be used include locust bean gum, guar gum, carrageenans, alginates, modified celluloses, beta-glucans, glucomannans and the like.

The viscous polysaccharides of the invention are branched or non-branched polymers of monosaccharides. A variety of monosaccharide subunits can be present in the viscous polysaccharides of the invention including arabinose, fructose, glucose, glucosamine, glucuronic acid, galactose, galactosammine, mannose, N-acetylmuramic acid, N-acetylneuraminic acid, rhamnose, xylose and the like. Such viscous polysaccharides can have a single type of monosaccharide subunit, e.g. only glucose, or a mixture of a variety of monosacharide subunits.

The covalent linkages connecting the monosaccharide subunits are generally beta (β) glycosidic linkages, although a small number of alpha (α) glycosidic linkages can be present, for example, at branch points. Examples of linkages that exist between the monosaccharides include 1→2 beta-glycosidic bonds, 1→3 beta-glycosidic bonds, 1→4 beta-glycosidic bonds, 1→6 beta-glycosidic bonds.

In one embodiment, the viscous polysaccharide is a water-soluble, cellulose-like polysaccharide. Such water-soluble cellulose-like polysaccharides include polymers of glycosides having either 1→3 or 1→4 beta-glycosidic bonds, or a mixture of 1→3 and 1→4 beta-glycosidic bonds.

The cellulose-like polysaccharides used in the invention have a mixture of 1→3 and 1→4 beta-glycosidic bonds and/or have only 1→3 or 1→4 beta-glycosidic bonds with various substituents in place of the hydroxyl groups found on cellulose so that the cellulose-like polysaccharide is soluble in aqueous solution. Beta-glucans have mixed 1→3 and 1→4 beta-glycosidic bonds and are found in natural materials such as oats and barley.

Examples of the structures of cellulose, with 1→4 beta-glycosidic bonds, and of beta-glucan, with a mixture of 1→3 and 1→4 beta-glycosidic bonds, are provided below, where a portion of each structure is illustrated.

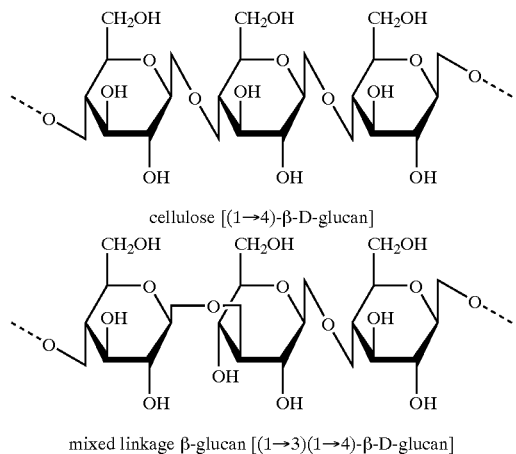

cellulose [(1→4)-β-D-glucan]

mixed linkage β-glucan [(1→3)(1→4)-β-D-glucan]

Cellulose is a natural beta-glycosidic polymer having 1→4 beta-glycosidic bonds where substantially all of the glycosidic subunits are substituted with hydroxyl groups. However, cellulose tends to be insoluble in aqueous solution. Accordingly, unmodified cellulose is preferably not used in the compositions and methods of the invention.

In contrast, the viscous polysaccharides of the invention are water-soluble. "Water soluble" for purposes of this application means that 2 grams of powdered viscous polysaccharide can be dispersed by stirring into 100 grams of water at a temperature between 0° C.–100° C. to provide a substantially clear, stable aqueous composition or dispersion, when the dispersion is brought to a temperature of about 20° C.

Water-soluble cellulose-like materials with 1→4 beta-glycosidic bonds that contain lower alkyloxy or hydroxy (lower(alkyloxy)) substituents can also be used in the compositions and methods of the invention. Similarly, water-soluble cellulose-like materials with 1→3 beta-glycosidic bonds, or a mixture of 1→3 and 1→4 beta-glycosidic bonds, that have lower alkyloxy or hydroxy (lower(alkyloxy)) substituents can be used. Such alkyloxy substituents preferably have one to four carbon atoms (i.e. $C_1$ to $C_4$ alkyloxy substituents). Preferred substituents include methoxyl and hydroxypropyloxyl groups. Cellulose-like polysaccharides with lower alkyloxy or hydroxy (lower(alkyloxy)) substituents are described in U.S. Pat. Nos. 4,900,573, 4,734,285, 4,704,285, and in Kirk-Othmer-Concise Encyclopedia of Chemical Technology, M. Grayson, ed., Wiley-Interscience NY (1985) at pages 231–232, the disclosures of which are incorporated herein by reference.

Representative water-soluble cellulose-like polysaccharides used in the invention are therefore of Formula I:

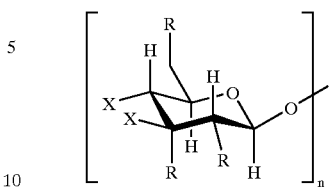

where
each R is separately a hydroxy, lower alkyloxy, or hydroxy (lower(alkyloxy)) group;
n is an integer ranging from about 500 to about 2500; and
X is an R group or a covalent bond to the oxygen at the first position of the adjacent β-glycoside.

Many such water-soluble cellulose-like polysaccharides are commercially available, or can be readily obtained via conventional organic synthetic methodology. Examples of the water-soluble cellulose-like polysaccharides that can be used in the invention are methylcellulose, hydroxypropyl methylcellulose or 2-hydroxypropyl methylcellulose, 2-hydroxyethyl methylcellulose, 2-hydroxybutyl methylcellulose, 2-hydroxyethyl ethylcellulose, 2-hydroxypropyl cellulose, methyl ethylcellulose, and 2-hydroxyethylcellulose. Water-soluble β-glucan and hydroxypropyl methylcellulose are examples of preferred compounds for the compositions and methods of the invention. A portion of the structure of hydroxypropyl methylcellulose is provided below.

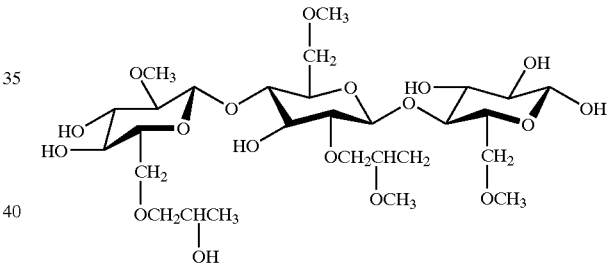

The invention provides methods of reducing body fat percentages and/or leptin serum levels in a mammal by administering to the mammal a viscous polysaccharide in an amount and for a time sufficient to reduce the percentage of body fat and/or leptin serum levels.

"Mammal" refers to any animal classified as a mammal, including humans, domestic and farm animals, nonhuman primates, and zoo animals, sports animals, or pet animals, such as dogs, cats, horses, cows, etc.

A time sufficient for reducing the percentage of body fat and/or leptin serum levels can vary depending on the level and duration of intestinal viscosity achieved, the amount of viscous polysaccharide consumed, the general health of the mammal, the level of activity of the mammal and related factors. However, with routine administration or consumption of a viscous polysaccharide of the invention, the percentage of body fat and the level of leptin in the blood generally begins to decrease within about two to about ten weeks, often within about three weeks to about eight weeks and particularly within about four to six weeks.

The viscous polysaccharides of the invention can be administered or consumed indefinitely. Accordingly, there is no precise upper limit on the amount of time during which the viscous polysaccharides can be consumed. The decision to stop consuming viscous polysaccharides can therefore be based upon whether the desired percentage body fat and/or leptin serum levels have been reached. In general, it may be beneficial to administer or consume an appropriate amount of the viscous polysaccharides of the invention for about twelve weeks, preferably about sixteen weeks, more preferably about twenty weeks. Moreover, even when the desired level of body fat or serum leptin has been achieved, one may choose to continue administration or consumption of a adequate amounts of viscous polysaccharide to help maintain the desired level of body fat and/or leptin levels.

Accordingly, the time for administration and/or consumption of the viscous polysaccharides of the invention can be varied to suit the needs of the person or mammal receiving the polysaccharides. In particular, because the polysaccharides of the invention are non-toxic and non-nutritive, the beneficial effects of administration can be realized by sustained or even indefinite administration or consumption of such polysaccharides.

Although viscous polysaccharides have been used in a variety of foodstuffs to improve certain functional properties, such as emulsification, texture or moisture retention, the amounts used are usually less than 0.5% of the foodstuff. These levels are generally too low to have a significant physiological effect on leptin levels and body fat percentages.

Therefore, the present invention also provides compositions and processed foodstuffs intended for mammalian ingestion that comprise an amount of viscous polysaccharides effective to lower the percentage of body fat or the amount of leptin in the bloodstream. Such compositions or foodstuffs can be consumed alone or in combination with other foods to meet the daily caloric requirements of the mammal. Preferably, the viscous polysaccharides of the invention are administered or consumed in sufficient amounts throughout the day, rather than in a single dose or amount.

In contrast to the small amounts employed in commercially available compositions and processed foodstuffs, the compositions and foodstuffs that are the subject of the present invention preferably comprise about 2 to about 20 weight percentage of one or more viscous polysaccharide, preferably about 3 to about 15 weight percentage, more preferably about 4 to about 12 weight percentage viscous polysaccharide(s). At these levels, about 3 g to about 20 g, preferably about 4 g to about 15 g, more preferably about 5 g to about 12 g, even more preferably about 6 g to about 10 g of viscous polysaccharides are ingested daily by a large mammal such as a human.

Therefore, to achieve a useful leptin-lowering or body fat percentage-lowering effect, an adult would ingest about 1 g to about 5 g per meal, preferably about 1.5 g to about 4 g per meal, and more preferably about 2 g to about 3 g per meal of a viscous polysaccharide, such as a beta-glucan or hydroxypropyl methylcellulose. However, dosages can vary and can be even higher for some human patients with highly elevated leptin or body fat levels.

The apparent viscosity of aqueous solutions of the viscous polysaccharides of this invention is proportional to the molecular weight or chain length of the compound. However, the average viscosity of an aqueous solution of the viscous polysaccharides of the invention is also directly proportional to the concentration of polysaccharide present in the solution. Hence, the viscosity of a composition or foodstuff can be adjusted by modulating either the molecular weight of the polysaccharide or the concentration of the polysaccharide.

The viscosities reported herein are measured in centipoises (cps) or centpoise (cP) or Pascal seconds (P·s) or milliPascal seconds (mPa·s), where 10 centipoise is 1 Pascal second. To obtain such viscosity measurements, a 1 or 2% by weight aqueous solution of polysaccharide at 20° C. can be measured in a rotational viscometer. The viscosity of 2% aqueous solutions of polysaccharide employed in the invention is desirably in the range of about 50 cps to about 200,000 cps, and preferably in the range of about 75 to about 100,000 cps, most preferably within the range of about 100 to about 10,000 cps. A "high viscosity" polysaccharide possesses a viscosity of at least 10,000 cps.

The average molecular weight of polysaccharide useful in lowering the leptin or body fat levels in mammals is at least about 10,000 daltons. If the viscosity is adjusted by modulating the molecular weight, the molecular weight can be increased. For example, the molecular weight can be increased to at least about 25,000 daltons, and preferably at least about 50,000 daltons. In some embodiments, the molecular weight can range from about 100,000 to about 250,000 daltons. The weight average molecular weight will be 3–10 times the number average molecular weight.

Many of the cellulose-like polysaccharides for use in the invention are available to one of skill in the art. For example, HPMC can be purchased under the trade name METHOCEL™ from Dow Chemical, Midland, Mich. Cellulose-like polysaccharides for use in the invention can also be made by the reaction of cellulose pulp with various chemical reactants in the presence of caustic soda. For example, methylcellulose can be made by reacting chloromethane with cellulose pulp and HPMC can be made using propylene oxide and chloromethane as reactants. For example, see C. R. Noller, Chemistry of Organic Compounds, W. B. Saunders Co., London (2d ed. 1957) at pages 404–405.

The polysaccharides of the invention can be administered in solution or in powder form, or may be combined with other food ingredients. Preferably, the polysaccharides of the invention are administered in combination with food or as a foodstuff. However, the polysaccharides of the invention can also be administered as pharmaceutical compositions. Pharmaceutical compositions containing the polysaccharides of the invention can be administered with a pharmaceutically acceptable carrier in a pharmaceutical unit dosage form. Pharmaceutically acceptable carriers include tableting excipients, gelatin capsules, or carriers such as a polyethylene glycol, a natural gel, and the like. Pharmaceutical unit dosage forms include tablets, capsules, gelatin capsules, pre-measured powders, pre-measured solutions, and the like. Hence, the polysaccharides may be formulated as tablets, granules, capsules, suspensions and the like.

While the method of administration or consumption may vary, the polysaccharides are preferably ingested by a human as an ingredient of his or her daily diet. The polysaccharides can be combined with a liquid vehicle, such as water, milk, vegetable oil, juice and the like, or with an ingestible solid or semi-solid foodstuff. A number of foodstuffs are generally compatible with polysaccharides of the invention. Examples of such foodstuffs are disclosed by M. K. Weibel et al., U.S. Pat. No. 4,923,981, the disclosure of which is incorporated by reference herein.

For example, it may be mixed into foods such as milk shakes, milk shake mixes, breakfast drinks, juices, flavored drinks, flavored drink mixes, yogurts, puddings, ice creams, ice milks, frostings, frozen yogurts, cheesecake fillings, candy bars, including "health bars" such as granola and fruit bars, gums, hard candy, mayonnaise, pastry fillings such as fruit fillings or cream fillings, cereals, breads, stuffings, dressings and instant potato mixes. An effective amount of the present polysaccharides can also be used as a fat-substitute in salad dressings, frostings, margarines, soups, sauces, gravies, mayonnaises, mustards and other spreads.

Therefore, "food ingredients," as the term is used herein, includes those ingredients commonly employed in recipes for the above foodstuffs, including flour, oatmeal, fruits, milk, eggs, starch, soy protein, sugar, sugar syrups, vegetable oils, butter, emulsifying agents such as lecithin, and the like.

The viscous polysaccharides can be partially or fully hydrated before they are orally ingested. For example, the viscous polysaccharides may be dispersed in a sufficient amount of water, milk, juice, flavored water, hot chocolate, soy milk, cream, or other liquid to make a drink item that can be consumed to administer an effective amount of the present polysaccharides. The viscous polysaccharides may be dispersed in a sufficient amount of water to make a syrupy liquid that is then mixed with one or more food ingredients such as flours, oatmeal, cornmeal, rice, barley, wheat germ, and other cereal products to made a paste or dough, the latter being subsequently treated to create an appealing foodstuff by procedures such as baking, extruding, and the like, to provide edible foodstuffs. Of course, colorings and flavorings may be added as may be appropriate to add to the attractiveness of the foodstuff. Food ingredients with which the viscous polysaccharides may be combined can be metabolizable and can have predetermined caloric values to create a diet item, diet drink or diet bar.

Therefore, in one embodiment the invention provides a composition comprising a food, drink or snack item, such as a cereal, milkshake or health bar, for reducing the percentage of body fat in a mammal comprising functionally effective amount of a viscous polysaccharide.

In another embodiment the invention provides a composition comprising a food or snack item, such as a cereal or health bar, for reducing the level of leptin in the plasma of a mammal comprising functionally effective amount of a viscous polysaccharide.

A functionally effective amount of viscous polysaccharide is employed as described above.

Preferably the reduction of body fat levels is about 5% to about 30%, although this amount can be varied depending on the amount and duration of administration of the viscous polysaccharide. More preferably, the reduction in body fat levels is about 10% to about 20%.

Leptin plasma levels can be reduced similarly. Hence, the level of leptin in the blood can be reduced by about 5% to about 50%, preferably about 10% to about 40% and more preferably about 15% to about 35%.

The desired dosage or amount of viscous polysaccharides that can be included in the diet will vary depending on the size and sex of the human patient as well as the patient's leptin levels and/or percent body fat. For example, the foodstuffs and food items described above will typically be formulated to comprise from about 2% to about 20% of total polysaccharide, depending on the viscosity grade polysaccharide used and the type of foodstuff or food item. Combinations of concentration and viscosity would have to be determined experimentally to some extent. For example, in a milk shake or pudding, the weight percentage can be 10 to about 20%. However, in baked goods, a lesser amount ranging from, for example, about 2% to about 5% by weight, might be preferred to avoid possible negative effects on the rheological characteristics of the product. Of course, the amount of viscous polysaccharide incorporated into a pharmaceutical unit dosage form can be much higher, since taste and rheology are not primary considerations, e.g., from about 20–98%, preferably about 50–80% of polysaccharide can be used. For 1000 g food the amount of viscous polysaccharide can range from about 20 g to about 200 g, preferably about 30 g to about 150 g, more preferably about 35 g to about 125 g of viscous polysaccharides are present per 1000 g food.

The present invention is further described by the following non-limiting examples.

EXAMPLE

Viscous Polysaccharide Consumption Decreases Percent Body Fat

In this example, rats were fed a variety of diets containing different types of water-soluble viscous polysaccharides. After four weeks, rats fed high viscosity β-glucan, or either low or high viscosity hydroxypropylmethylcellulose had significantly lower body fat levels.

Materials and Methods

Animals

The animal-use protocol was approved by the University of Minnesota Animal Care Committee. Fifty Wistar rats (initially around 80–90 g) were purchased from Harlan Sprague-Dawley, Inc (Indianapolis, Ind., USA).

The rats were individually housed in wire bottom cages in a temperature controlled animal room with a daily photoperiod of twelve hours of light and twelve hours of dark, with light from 1800 to 0600.

Upon arrival, animals were fed one of the five experimental diets for four weeks. Body weight and 24 hour-food intake were determined weekly for the four weeks that the experimental diets were fed.

The rats were provided the diets and water ad libitum.

Diets

The diets were all nutritionally complete and were based on the AIN-93 G diet (Reeves et al. 1993). All diets contained 20% of protein, 15% of fat and 0.12% of cholesterol. Five diets were prepared that differed only by the type of polysaccharide added, as follows:

Cellulose (CE) (control diet)

Beta-Trim (beta glucan) low viscosity (BT-LV)

Beta-Trim (beta glucan) high viscosity (BT-HV)

Hydroxypropyl methylcellulose (HPMC) low viscosity (HPMC-LV)

Hydroxypropyl methylcellulose (HPMC) high viscosity (HPMC-LV)

The composition of these diets is given in Table 1.

TABLE 1

Composition of diets containing Cellulose, Beta-Glucan or HPMC for 1 kg of diet

| Diet | Cellulose (g) | Beta-glucan LV (g) | Bet-aglucan HV (g) | HPMC LV (g) | HPMC HV (g) |
| --- | --- | --- | --- | --- | --- |
| Cornstarch | 347 | 272.3 | 287 | 347 | 347 |
| Casein | 200 | 195.6 | 193.6 | 200 | 200 |
| Dextrinized cornstarch | 115.2 | 115.2 | 115.2 | 115.2 | 115.2 |
| Sucrose | 87.3 | 87.3 | 87.3 | 87.3 | 87.3 |
| Corn oil | 150 | 150 | 150 | 150 | 150 |
| Cellulose | 50 | 29.1 | 16.4 | 10 | 10 |
| Mineral mix | 35 | 35 | 35 | 35 | 35 |
| Vitamin mix | 10 | 10 | 10 | 10 | 10 |
| L-Cystine | 3 | 3 | 3 | 3 | 3 |

TABLE 1-continued

Composition of diets containing Cellulose, Beta-Glucan or HPMC for 1 kg of diet

| Diet | Cellulose (g) | Beta-glucan LV (g) | Bet-aglucan HV (g) | HPMC LV (g) | HPMC HV (g) |
|---|---|---|---|---|---|
| Choline bitartrique | 2.5 | 2.5 | 2.5 | 2.5 | 2.5 |
| BHT* | 0.014 | 0.014 | 0.014 | 0.014 | 0.014 |
| Cholesterol* | 1.2 | 1.2 | 1.2 | 1.2 | 1.2 |
| Beta trim 12% | 0 | 100 | 0 | 0 | 0 |
| Beta-trim 20% | 0 | 0 | 100 | 0 | 0 |
| HPMC K100 | 0 | 0 | 0 | 40 | 0 |
| HPMC K4M | 0 | 0 | 0 | 0 | 20 |
| HPMC K15M | 0 | 0 | 0 | 0 | 20 |

*BHT and cholesterol were added directly diluted to the corn oil.

The HPMC formulations were prepared from different HPMC grades. The low viscosity HPMC was K100 and the high viscosity HPMC mixture was 50% K15M and 50% K4M. At 25° C., two percent solutions of the different HPMC grades have the following viscosities: K100 viscosity is 100 mPa·s; K4M viscosity is 4000 mPa·s; and K15M viscosity is 15,000 mPa·s.

The appropriate formulations have been determined according to previous studies in the lab to examine the correlation between in vivo and in vitro viscosity (unpublished).

Two diets contained BetaTrim (Quaker Oats, Inc) as a beta-glucan source: a 12% BetaTrim diet (10% of diet) and a 20% BetaTrim diet (10% of diet). For these diets, the addition of BetaTrim increased the amount of carbohydrates and protein according to the composition of the BetaTrim (4.4% of protein and 74.4% of starch in 12% BetaTrim and 6.4% of protein and 60.0% of starch in 20% BetaTrim). So, in order to normalize the nutritional content of these diets to match that of the AIN-93 G diet, we compensated by lowering the quantity of casein to obtain a final total of 20% of protein. Cornstarch was used to balance the carbohydrate quantity, while sucrose and dextrinized cornstarch stayed the same.

Two diets contained HydroxyPropylMethylCellulose (HPMC), (METHOCEL, The Dow Chemical Company, Midland, Mich., USA) as polysaccharide source (4% of diet). The amount of cornstarch and casein for these diets was held constant.

Cellulose was used in a control diet, instead of the BetaTrim or the HPMC used in the test diets. However, cellulose was also added to the test diets to make up for the lesser weight percentage of the BetaTrim and HPMC. The amount of cellulose added to 1000 g of the four test diets was determined by adding all the other constituents together except cellulose and subtracting this amount from 1000 g.

Tissue Collection

Rats were fasted overnight before being taken. The following morning, they were anesthetized with ether and blood samples for leptin assay were drawn by cardiac puncture into tubes containing EDTA. Plasma was prepared and stored at −70° C.

The abdominal cavity was opened. The small intestine was removed, the contents were collected in tubes and kept on ice. Then epididymal and retroperitoneal fad pads were removed and weighed. Livers were removed, weighed, and two grams were collected for microsomes preparation. The remainder of the livers were wrapped in plastic bags and quickly frozen for cholesterol measurement. The two femurs were removed, one for calcium content measurement and the other one for bone density measurement, and wrapped in plastic bags and frozen.

Plasma Leptin Level

Serum was stored at −70° C. until hormone assay was performed. Plasma leptin level was determined in duplicate by a commercial radioimmunoassay kit using $^{125}$I-labeled rat leptin antiserum (Linco Research, St Charles, Mo.).

Liver Cholesterol Analysis

Samples for liver cholesterol analysis were prepared according to the method of Folch et al. (1957) for lipids extraction, modified and applied to liver. Lipids were extracted from approximately 1 g (exact weight known) of liver. Samples were homogenized and rinsed with chloroform:methanol (2:1) (total 20 mL), filtered through a filter paper, mixed with a 6 mL of 0.9% NaCl solution and centrifuged. The lower phase was kept and evaporated under $N_2$. Samples were reconstituted in 10 mL chloroform:methanol.

Cholesterol assay was performed on 10 uL using a commercial kit (Infinity™ cholesterol reagent, Sigma Diagnostics, St. Louis, Mo.).

Intestinal Content Supernatant Viscosity Measurement

After fasting overnight, animals were fed 7.5 g of diet and allowed 2½ hours for consumption and digestion. The precise amount of diet consumed was recorded. Once the small intestine removed, the contents were stripped out in tubes and centrifuged at 30° C. and 19,500 g for 45 minutes. Then, supernatant was collected and the viscosity of 0.5 ml of sample was measured at 37° C. with a Brookfield-Wells Coneplate viscometer, model LVT-CP (CP-51 cone). Measurements were taken at shear rates, then viscosity versus shear rate was plotted on a log-log scale and viscosity was estimated by extrapolation of the line to a shear rate of 23.0 $s^{-1}$.

Bone Density Determination

The bone density was measured using the method of Archimedes' principle (Keenan et al. 1992, Keenan et al. 1997). The bones were cleaned and hydrated by immersion in distilled water under vacuum for one hour (bone is porous and air in bone must be displaced by immersion in distilled water). Bones were weighed twice with a micro electrobalance (Cahn), first out of water, and then submerged in water. The density was calculated using the formula:

$$P_{bone}=A/(A-B)*P_w$$

where $P_{bone}$ is the density of the bone, $P_w$ is the density of distilled water at known temperature, A is the weight of the hydrated bone out of water, B is the weight of hydrated bone submerged in water and A−B is the difference of weight equivalent to the weight of volume displaced by the bone, equivalent of the volume of the bone.

Bone Calcium Content

Calcium in bones was measured by atomic absorption analysis. Bones were ashed for 12 hours at 485° C. Ashes were diluted in 5 mL of 20% trace metal free HCl, then 5 mL of distilled water. Supernatant was removed after ashes settled and diluted 1000 times with 0.5% lanthanum chloride. A Perkin-Elmer flame atomic absorption spectrometer was used to analyze samples for calcium content.

Statistical Analysis

Values were expressed as means±standard error. The significance of differences was analyzed by one-way ANOVA performing PROC GLM in SAS statistical software (SAS Institute 1999). Duncan's multiple range test was used to detect differences among the groups. A significant difference was accepted at $p<0.05$.

RESULTS

Intestinal Content Supernatant Viscosity

The intestinal contents supernatant viscosities are shown on Table 2. As can be seen, the BT-HV group's viscosity is much lower than the HPMC-HV diet's viscosity in spite of the attempt to match their viscosities. The BT-LV, BT-HV, HPMC-LV, and HPMC-HV diets increased significantly the intestinal viscosity compared to the cellulose and BT-LV diets ($p<0.05$). The viscosities of the two HPMC diets are not significantly different ($p>0.05$).

TABLE 2

Final Body weight, Peritoneal and Epididymal Fat Pads Weights, and % of fat pads in body weight of rats fed diets cellulose, high and low viscosity Beta glucan and high and low viscosity HPMC

| Dietary group | Intestine Viscosity (mPa · s) | Final body weight (g) | Retroperitoneal fat pad weight (g) | Epidydimal fat pad weight (g) | % of fat pads in body weight |
|---|---|---|---|---|---|
| Cellulose | 8.2[a] | 313.00[a] | 2.35[a] | 2.17[a] | 2.87[a] |
| Beta glucan LV | 533.6[b] | 299.09[ab] | 2.22[ab] | 2.06[ab] | 2.83[a] |
| Beta glucan HV | 997.6[b] | 285.82[b] | 1.64[c] | 1.65[c] | 2.28[b] |
| HPMC LV | 2082[c] | 300.91[ab] | 1.76[bc] | 1.83[abc] | 2.36[b] |
| HPMC HV | 2163.3[c] | 293.09[ab] | 1.51[c] | 1.73[bc] | 2.19[b] |

Body Weight and Fat Pad Weights

The final body weights of the animals for the 5 different diet groups are shown Table 2.

As illustrated by Table 2, there is no significant difference in body weight except between cellulose and BT-HV groups ($p<0.05$). There were no significant differences in food intake among the five groups, although there was a trend for a lower food intake in the BT-HV group.

The % of fat pads is an index of the % of body fat mass. Table 2 shows fat pads weights and the % of fat pads weight in body weight for each diet group. Fat pad weight decreased when viscosity increased for the two kinds of fat pads, although the effect is more apparent for retroperitoneal fat pads. The BT-LV diet did not have a significant effect on the fat pads weight, but for the rats fed the two HPMC diets the fat pads weights are significantly lower ($p=0.092$ for epididymal fat pad and $p=0.008$ for retroperitoneal fat pad). The % of fat pads of body weight is an index of the % of body fat mass. This % is negatively correlated with viscosity ($r^2=0.73$) (FIG. 1). The % of fat pads in body weight for the BT-HV, HPMC-LV, HPMC-HV diets fed animals represent reductions of 20%, 18% and 24% of the % of fat pads weight in body weight compared to the cellulose diet.

Liver Cholesterol Concentration

Table 3 provides the liver cholesterol concentrations for each of the 5 diets, along with the intestinal viscosity, plasma leptin concentrations, bone density and bone calcium concentrations.

TABLE 3

Intestine viscosity, Liver cholesterol concentration, plasma leptin concentration corrected by body weight, bone density and bone calcium content in rats fed cellulose, Beta glucan low and high viscosity, and HPMC low and high viscosity diets

| Dietary group | Intestine Viscosity (mPa · s) | Liver Cholesterol Concentration (mg/g) | Plasma Leptin Concentration, corrected by body weight (g) | Bone Density | Bone Calcium Concentration (mg/g) |
|---|---|---|---|---|---|
| Cellulose | 8.2[a] | 11.89[a] | 11.02[a] | 1.380[a] | 230.17[a] |
| Beta-glucan LV | 533.6[b] | 8.10[b] | 12.68[a] | 1.391[a] | 240.01[a] |
| Beta-glucan HV | 997.6[b] | 7.46[b] | 9.56[ab] | 1.380[a] | 233.54[a] |
| HPMC-LV | 2082.0[c] | 7.41[b] | 6.68[b] | 1.366[ab] | 221.65[a] |
| HPMC-HV | 2163.3[c] | 7.82[b] | 6.90[b] | 1.345[b] | 199.89[b] |

Values in the same column with different superscripts are significantly different ($p<0.05$).

For each of the BT or HPMC diet-fed groups, there was a significant hypocholesterolemic effect in the liver compared to the cellulose diet-fed group ($p=0.0001$). However, between the two BT diet-fed groups, the difference was not statistically significant, nor was the difference statistically significant between the two HPMC diet-fed groups or between BT groups and HPMC groups.

Liver cholesterol concentration was highly correlated with the log of intestinal contents supernatant viscosity ($r^2=0.95$).

Plasma Leptin Concentration

Figure 2:
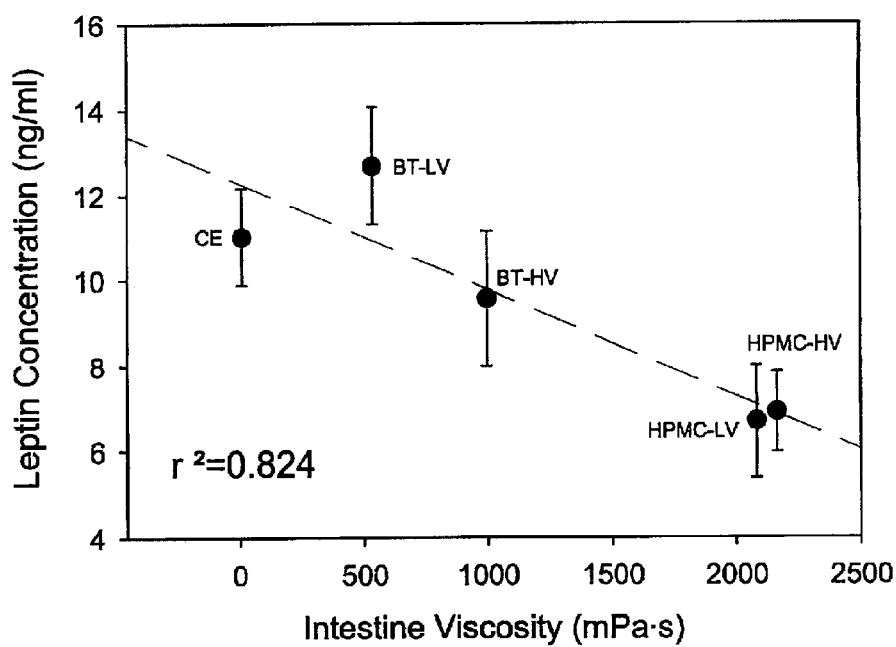
FIG. 2 graphically illustrates the relationship between plasma leptin concentration and the viscosity of a supernatant of the intestinal contents of rats. As illustrated, there is a negative correlation between the intestinal viscosity and the concentration of leptin in the plasma, indicating that leptin concentration decreases as the viscosity of the diet increases.
Figure 3:
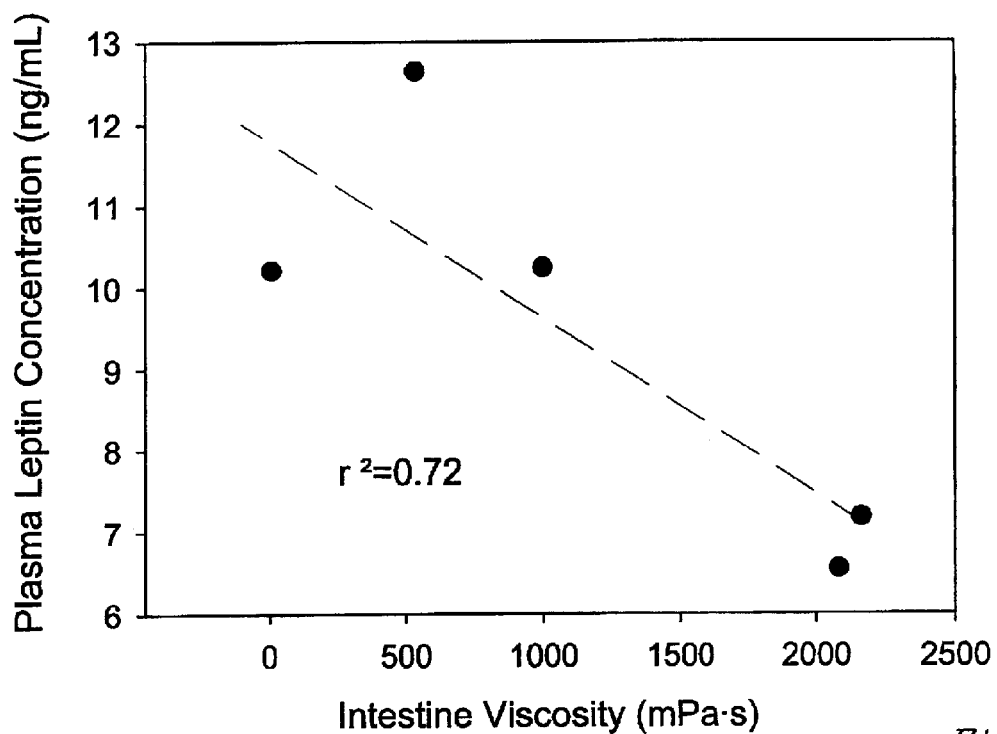
FIG. 3 graphically illustrates the relationship between plasma leptin concentration and the viscosity of a supernatant of the intestinal contents of rats. As illustrated, there is a negative correlation between the intestinal viscosity and the concentration of leptin in the plasma, indicating that leptin concentration decreases as the viscosity of the diet increases.
Figure 6:
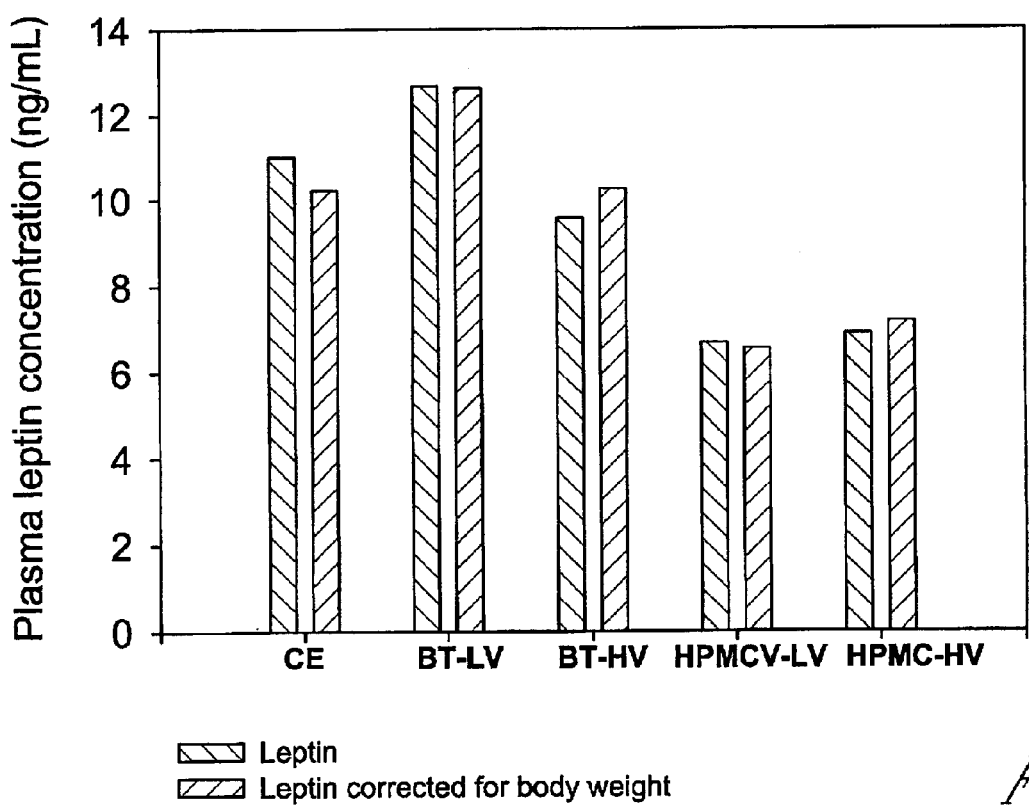
FIG. 6 is a bar graph illustrating the relationship between plasma leptin concentration and the type of diet, before and after correction for body weight. The five diet types differed only in the type of polysaccharide fiber added: Cellulose (CE, control diet); Beta-Trim (beta glucan) low viscosity (BT-LV); Beta-Trim (beta glucan) high viscosity (BT-HV); Hydroxypropyl methylcellulose (HPMC) low viscosity (HPMC-LV); and Hydroxy-propyl methylcellulose (HPMC) high viscosity (HPMC-LV). As illustrated, the high and low viscosity HPMC diets lead to lower concentrations of leptin in the plasma.

As shown in Table 3, the plasma leptin concentration is significantly reduced in the groups fed HPMC, and there was a trend for a reduction in the BT-HV group. A bar graph illustrating the plasma leptin concentration for animals fed the different diets is provided in FIG. 6. Indeed, there was a high inverse correlation between plasma leptin concentration and intestinal contents supernatant viscosity ($r^2=0.82$) (FIG. 2), which was slightly reduced when plasma leptin values were statistically corrected for body weigh ($r^2=0.72$) (FIG. 3).

Figure 4:
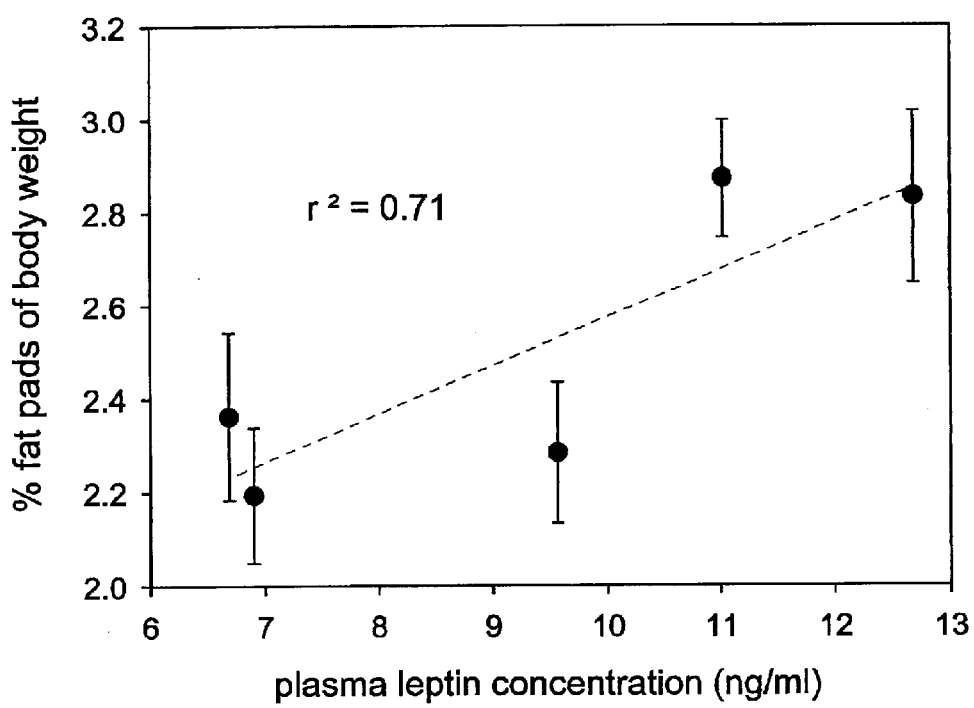
FIG. 4 graphically illustrates the relationship between plasma leptin concentration and the percent fat pads of body weight of rats. As illustrated, there is a positive correlation between percent fat and the concentration of leptin in the plasma, indicating that lower leptin concentrations are correlated with lower body fat.
Figure 5:
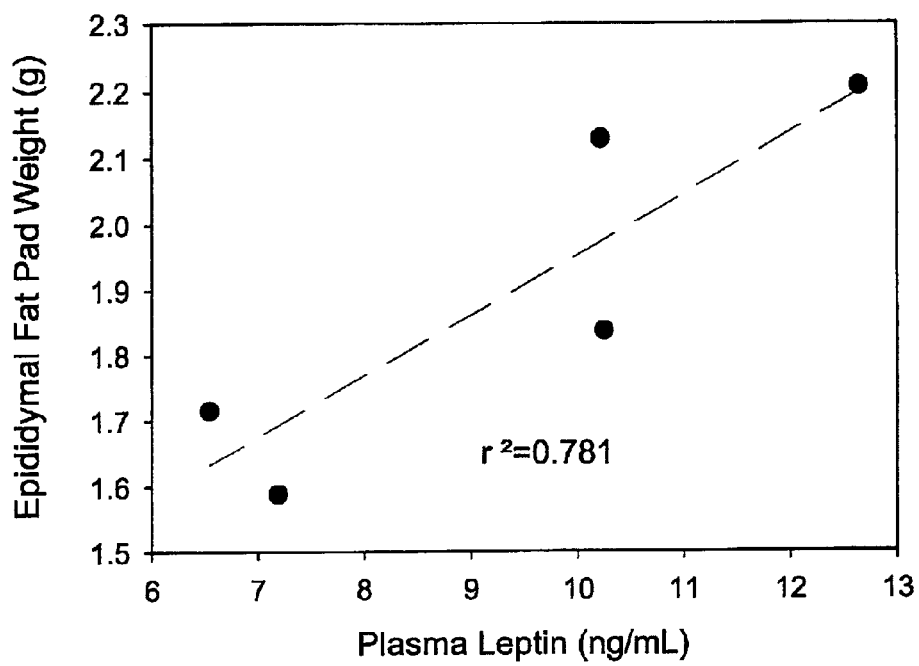
FIG. 5 graphically illustrates the relationship between plasma leptin concentration and the percent epididymal fat of body weight of rats, after correction for body weight. As illustrated, there is a positive correlation between the percent epididymal fat and the concentration of leptin in the plasma, indicating that body fat increases as leptin concentration increases.
Figure 7:
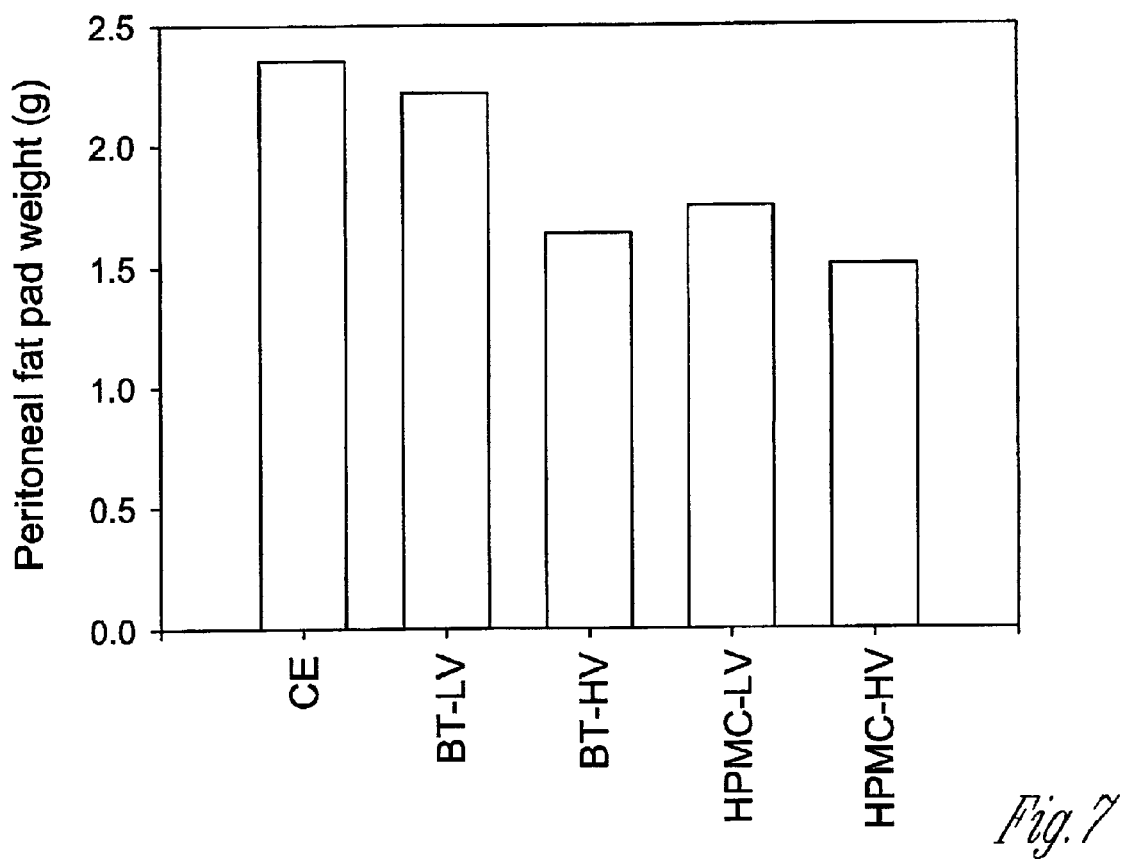
FIG. 7 is a bar graph illustrating the relationship between retroperitoneal fat pad weight and the type of diet. The five diet types differed only in the type of polysaccharide fiber added: Cellulose (CE, control diet); Beta-Trim (beta glucan) low viscosity (BT-LV); Beta-Trim (beta glucan) high viscosity (BT-HV); Hydroxypropyl methylcellulose (HPMC) low viscosity (HPMC-LV); and Hydroxy-propyl methylcellulose (HPMC) high viscosity (HPMC-LV). As illustrated, the high viscosity Beta-Trim (beta glucan) diet and the high and low viscosity HPMC diets lead to lower retroperitoneal body fat.

Plasma leptin concentration was also highly correlated with the % of fat pads in body weight ($r^2=0.71$) (FIG. 4). Similarly, plasma leptin concentration was highly correlated with the % of epididynal fat pad in body weight ($r^2=0.781$) (FIG. 5). A bar graph illustrating the peritoneal fat pad weight for animals fed the different diets is provided in FIG. 7.

Bone Density and Calcium

Bone density (Table 3) was significantly lower for animals fed high viscosity HPMC diets compared to the animals fed the cellulose diet or the low or high BT diets. Bone density was also positively correlated with plasma leptin concentration ($r^2=0.75$) (figure not shown).

The bone calcium concentration for the 5 groups is shown in Table 3. The bone calcium concentration of the HPMC-HIV group was significantly lower than the other groups. The bone calcium content and bone density were highly correlated ($r^2=0.98$), as expected (figure not shown).

These data indicate that the low viscosity HPMC diet may be the best diet because this diet causes a decrease in percent body fat, lower plasma cholesterol levels and lower leptin plasma concentrations without significant adverse effects on bone density. The high viscosity HPMC diet also has beneficial effects but tends to have a negative effect on bone density. The lower HV HPMC bone density was not necessarily related to lower leptin concentrations because the LV HPMC diet gave rise to even lower leptin concentration without such a negative bone density effect. The negative effect on bone density may therefore be countered by calcium supplements.

The high viscosity beta-glucan diet also has positive effects on body fat and cholesterol, as well as a positive effect on leptin concentrations without much effect on bone density.

What is claimed:

1. A method of reducing the level of leptin in the bloodstream of a mammal comprising administering a sufficient amount of viscous, water-soluble, non-nutritive, non-starch, indigestible polysaccharide to the mammal for a time sufficient to reduce the level of leptin in the bloodstream of the mammal, wherein the sufficient amount of the polysaccharide is about 2% to about 20% of total polysaccharide in the mammal's diet, the polysaccharide is a polymer of monosaccharides substantially connected by beta (β) glycosidic linkages, and a 2% aqueous solution of the polysaccharide has a viscosity of about 50 cps to about 200,000 cps.

2. The method of claim 1, wherein the method reduces the percentage of body fat in a mammal.

3. The method of claim 2 where the percentage of body fat is reduced by about 5% to about 40%.

4. The method of claim 2 where the percentage of body fat is reduced by about 10% to about 30%.

5. The method of claim 2 where the percentage of body fat is reduced by about 15% to about 25%.

6. The method of claim 1 wherein the monosaccharides are arabinose, fructose, glucose, glucosamine, glucuronic acid, galactose, galactosammine, mannose, N-acetylmuramic acid, N-acetylneuraminic acid, rhamnose, xylose or a mixture thereof.

7. The method of claim 1 wherein the beta glycosidic linkages are 1→2 beta-glycosidic bonds, 1→3 beta-glycosidic bonds, 1→4 beta-glycosidic bonds, 1→6 beta-glycosidic or a mixture thereof.

8. The method of claim 1 wherein the beta glycosidic linkages are 1→3 beta glycosidic linkages or 1→4 beta glycosidic linkages, or a mixture of 1→3 and 1→4 beta-glycosidic linkages.

9. The method of claim 1 wherein the polysaccharide is locust bean gum, guar gum, carrageenan, alginate, modified cellulose, beta-glucan, or glucomannan.

10. The method of claim 1 wherein the polysaccharide has Formula I:

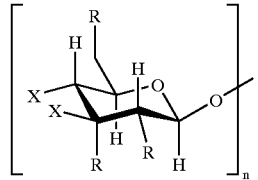

wherein
    each R is separately hydroxy, lower alkyloxy, or hydroxy (lower(alkyloxy));
    n is an integer ranging from about 500 to about 2500; and
    X is an R group or a covalent bond to the oxygen at the first position of the adjacent monosaccharide.

11. The method of claim 1 wherein the polysaccharide is methylcellulose, hydroxypropyl methylcellulose, 2-hydroxypropyl methylcellulose, 2-hydroxyethyl methylcellulose, 2-hydroxybutyl methylcellulose, 2-hydroxyethyl ethylcellulose, 2-hydroxypropyl cellulose, methyl ethylcellulose, or 2-hydroxyethylcellulose.

12. The method of claim 1 wherein the polysaccharide is β-glucan.

13. The method of claim 1 wherein the polysaccharide is hydroxypropyl methylcellulose.

14. The method of claim 1 wherein the sufficient amount of polysaccharide is an amount that provides an intestinal viscosity of about 1000 mPa·s to about 3000 mPa·s.

15. The method of claim 1 wherein the sufficient amount of polysaccharide is an amount that provides an intestinal viscosity of about 1500 mPa·s to about 2500 mPa·s.

16. The method of claim 1 wherein the sufficient amount of polysaccharide is about 1 g to about 5 g polysaccharide per meal.

17. The method of claim 1 wherein the sufficient amount of viscous polysaccharide is about 2 g to about 3 g polysaccharide per meal.

18. The method of claim 1 wherein the time sufficient for reducing the level of leptin in the bloodstream of a mammal is at least about two to at least about ten weeks.

19. The method of claim 1 wherein the time sufficient for reducing the level of leptin in the bloodstream of a mammal is at least about three weeks to at least about eight weeks.

20. The method of claim 1 wherein the time sufficient for reducing the level of leptin in the bloodstream of a mammal is at least about four to at least about six weeks.

21. The method of claim 1 wherein the polysaccharide is administered indefinitely.

22. The method of claim 1 where the level of leptin in the bloodstream of a mammal is reduced by about 5% to about 50%.

23. The method of claim 1 where the level of leptin in the bloodstream of a mammal is reduced by about 10% to about 40%.

24. The method of claim 1 where the level of leptin in the bloodstream of a mammal is reduced by about 15% to about 35%.

25. The method of claim 1 where the mammal is a human.

26. The method of claim 1 where the polysaccharide is administered in an applesauce, a cereal, a cookie, a cracker, a flavored drink, a fruit juice, an ice cream, a milk shake, a pudding or a snack bar.

27. The method of claim 1, wherein the method reduces the percentage of body fat in a mammal without substantially changing the mammal's weight.

28. The method of claim 1, wherein the method reduces the percentage of body fat in the mammal and wherein the polysaccharide gives rise to an intestinal viscosity of about 1000 mPa·s to about 3000 mPa·s.

29. The method of claim 1 wherein the method reduces the percentage of body fat in a mammal without substantially changing the mammal's food intake.

* * * * *